United States Patent [19]
Emilio et al.

[11] Patent Number: 5,814,047
[45] Date of Patent: Sep. 29, 1998

[54] INTRAMEDULLARY NAIL FIXATION APPARATUS AND ITS FIXATION METHOD

[75] Inventors: Tze-Hong Emilio, Keelung; Shan-Chang Chueh, Taipei; Ting-Hui Chiu; Chi-Ming Shih, both of Hsinchu; Chung-An Wu, Chia-Yi; Cheng-Kung Cheng, Taipei Hsien, all of Taiwan

[73] Assignee: Industrial Technology Research Institute, Hsinchu, Taiwan

[21] Appl. No.: 805,910

[22] Filed: Mar. 4, 1997

[51] Int. Cl.⁶ .................................................. A61B 17/72
[52] U.S. Cl. ................................................. 606/62; 606/73
[58] Field of Search ................................. 606/62, 63, 64, 606/65, 66, 67, 68, 72, 73, 60

[56] References Cited

U.S. PATENT DOCUMENTS

| | | | |
|---|---|---|---|
| 3,779,239 | 12/1973 | Fischer et al. | 606/63 |
| 4,781,181 | 11/1988 | Tanguy | 606/64 |
| 4,827,917 | 5/1989 | Brumfield | 606/64 |
| 5,057,103 | 10/1991 | Davis | 606/63 |
| 5,531,748 | 7/1996 | De La Caffiniere | 606/62 |
| 5,569,249 | 10/1996 | James et al. | 606/62 |
| 5,603,715 | 2/1997 | Kessler | 606/63 |

*Primary Examiner*—Guy V. Tucker
*Attorney, Agent, or Firm*—Bacon & Thomas

[57] ABSTRACT

An intramedullary nail fixation apparatus and its fixation method, the apparatus including a tubular intramedullary nail having a plurality of equiangularly spaced piercing points, and a plurality of flexible screws respectively mounted in the intramedullary nail and forced to fix the intramedullary nail to the marrow cavity of the bone to be fixed, each flexible screw having a rounded stem convenient for rotation, and a self-tapping screw tip at one end of the rounded stem convenient for being forced out of the intramedullary nail through one piercing point and then threaded into the wall of the bone upon rotation of the respective flexible screw. The invention relates also to the method of the fixation of the apparatus.

9 Claims, 7 Drawing Sheets

INTRAMEDULLARY NAIL FIXATION APPARATUS AND ITS FIXATION METHOD

BACKGROUND OF THE INVENTION

The present invention relates to an intramedullary nail fixation apparatus and the method of fixing same. The apparatus can be quickly installed to fix an intramedullary nail to the inside of a fractured bone, permitting the fractured bone to be cured within a short period of time.

The technology of fixing a metal intramedullary nail to the marrow cavity to cure a simple fracture or comminuted fracture has been well known. Taiwan Pat. Publication No. 202,584, entitled "INTERLOCKING intramedullary NAIL AIMING FRAME", discloses the application of an aiming device to guide screws into respective fixing positions. The intramedullary nail used in the aforesaid patent is an interlocking nail. This structure of interlocking nail has radial screw holes. When the interlocking nail is inserted into the marrow cavity of the bone to be fixed, screws are respectively threaded into the screw holes of the interlocking nail and the wall of the bone to fix the interlocking nail to the inside of the bone, so that the bone can be maintained in the desired length and prohibited from rotary motion. The aiming device disclosed in Taiwan Pat. Publication No. 202,584 is used to guide the screws into the screw holes of the interlocking nail. However, because the interlocking nail is inserted into the marrow cavity of the bone, it may be forced by the rigid bone to twist, causing a deviation of the screw holes of the interlocking nail from the aiming points of the aiming device.

U.S. Pat. No. 4,850,344 discloses an aiming apparatus for making transverse bores in a patient's bone in register with the holes or bores of an interlocking nail. The aiming apparatus comprises a holder for the accommodation of an aiming member adapted to be brought into the beam path of an X-ray apparatus, a reception head for receiving a drill rotatably supported in the holder, and a power drive supported by the holder for rotatably driving the reception head. This aiming apparatus is complicated to operate because it must be used with an X-ray apparatus. The use of an X-ray apparatus increases the chance of exposing the bodies of the patent and the aiming apparatus operator to X-rays.

U.S. Pat. No. 4,875,474 discloses an improved interlocking nail having variations in wall thickness along its length. The nail is provided with a longitudinal slot which extends along the entire length of the nail. The nail is also provided with transverse openings through the proximal and distal portions to receive interlocking screws, and a portion of the inside diameter of the proximal portion is threaded to provide a point of attachment for insertion of extraction devices. The installation of the interlocking nail still needs the use of an aiming apparatus and a X-ray apparatus.

U.S. Pat. No. 5,411,503 discloses an instrument for distal targeting of locking screws in intramedullary nails, in which a probe inserted into the intramedullary nail positions two electromagnetic drive coils with their magnetic axes parallel to and at a fixed offset from the axis of a transverse hole to be drilled; a hand-held guide, containing a drill bushing and four receiving coils with same offset as the drive coils, when moved about in the vicinity of the probe, produces a corresponding movement of graphical images on a display screen. The graphical images provide intuitive information as to how the guide must be moved to accurately align the drill bushing with the axis of the transverse hole. This method eliminates the use of an X-ray apparatus, and can accurately and quickly find and align the drill bushing with the axis of the transverse hole. However, the installation and operation cost of the probe, guide, image processing apparatus add extra expense. Furthermore, the guide must be operated by a skilled person so that it can be accurately allocated.

Furthermore, the locking screws used in the aforesaid interlocking nails generally have a head of thickness about 0.6 cm projecting outside the bone after the installation, and the projecting head will contact the skin and cause the patient to feel uncomfortable.

In clinical practice, the selection of an intramedullary nail must be determined subject to the type of the disease or fracture, the typical intramedullary nails, include the interlocking nail and the Kuntscher nail. The fixation of the Kuntscher nail eliminates the use of locking screws. These two types of nails have a great difference in cost. It may be difficult to make a selection between these two types of nails.

A conventional interlocking nail is generally equipped with two screws, which are perpendicularly threaded through the wall of the bone in the same direction. Because the bone bears the pressure at area around the screws, the concentration of stress tends to cause the screws to break. In order to fix the screws, an incision of about 7–10 cms must be made on the body of the patient near the bone to be fixed. When the intramedullary nail is installed and fixed in place by the screws, the incision must be sutured.

Further, according to the latest fracture curing concept, the connecting areas of the broken parts of the bone are preferably maintained in contact with each other to provide a proper value of contact force and some degree of microvibration, so that the broken bone can be cured within a short period of time. However, because rigid locking screws are commonly used to fix the interlocking nail, the parts of the broken bone cannot be maintained in good contact with each other. Therefore, a dynamization procedure shall be employed to remove the locking screws several months after the implantation of the interlocking nail. The features of the present invention are as follows:

1. Each flexible screw has a rounded stem convenient for rotation, and a self-tapping screw tip at one end of the rounded stem convenient for being forced out of the intramedullary nail through one piercing point and then threaded into the wall of tibia upon rotation of the respective flexible screw. Because the flexible screws are inserted through the tubular intramedullary nail from the inside to the outside radiately, no extra X-ray aiming procedure is needed, and only one incision of length about 5–7 cms is required near the proximal end of the bone for allowing the tubular intramedullary nail to pass into the marrow cavity of the bone.

2. When the flexible screws are fixed to the bone to secure the tubular intramedullary nail in place, only a tiny part of about 0.3 cm of each of the flexible screws are exposed to the outside of the bone, therefore the flexible screws do not hurt the muscles and the skin.

3. Because flexible screws are used to fix the tubular intramedullary nail in place, the non-union problem due to the use of rigid screws is eliminated, and no any further dynamization is required.

4. Because the flexible screws are equiangularly spaced from one another and extend to different lengths in the tubular intramedullary nail, the problem of concentration of stress is eliminated.

5. When to curing a simple fracture or comminuted fracture, the decision of fixing the flexible screws or removing them from the tubular intramedullary nail can be made after the insertion of the tubular intramedullary nail into the marrow cavity of the bone.

SUMMARY OF THE INVENTION

The present invention has been accomplished under the circumstances in view. The objects of the present invention and the measures of achieving such objects are outlined hereinafter.

(1) The prime object of the present invention is to provide an intramedullary nail fixation apparatus and its fixation method which shorten the operation time. This object is achieved by providing a tubular intramedullary nail equipped with flexible screws on the inside. The flexible screws are forced out of the intramedullary nail into the wall of the bone. Therefore, little time is needed to aim the screws and to fix them in place, and the positioning of the screws can be accurately achieved.

According to the method of the present invention, only one incision is needed for the passing of the intramedullary nail, permitting the intramedullary nail to be installed in the marrow cavity of the bone to be fixed, and the screws used for fixing the intramedullary nail to the bone are installed in the inside of the intramedullary nail and driven outwards through the wall of the intramedullary nail into the wall of the bone, therefore no second incision is required for the installation of the screws, and the total fixing time of the intramedullary nail takes only about 10 minutes, which is much shorter than conventional methods which commonly need about 30–60 minutes to aim the interlocking nail and the locking screws.

(2) Another object of the present invention is to provide an intramedullary nail fixation method which greatly improves the curing effect of the bone by means of a semi-rigid fixation procedure, which uses flexible screws to fix the intramedullary nail to the broken bone. The installation of the flexible screws permits the broken parts of the bone to be maintained in contact with each other so that a proper value of contact force and some degree of microvibration can be maintained, and no further dynamization is required.

(3) Still another object of the present invention is to provide an intramedullary fixation apparatus which is safe in use and gives no harm to the patient. Because the flexible screws are forced from the inside of the intramedullary nail to penetrate the wall of the intramedullary nail and then to thread into the wall of the bone, X-ray apparatus is not needed to aim the flexible screws and the risk of X-ray exposures is eliminated.

(4) Still another object of the present invention is to provide an intramedullary nail fixation apparatus which uses a tubular intramedullary nail equipped with flexible screws on the inside for the fixation of a simple fracture or comminuted fracture, and the flexible screws are locked or removed from the intramedullary nail after the insertion of the intramedullary nail into the marrow cavity of the bone. Therefore, the invention eliminates the problem of conventional implantation in determining the selection between an interlocking nail and a Kuntscher nail prior to surgical operation.

(5) A yet further object of the present invention is to provide an intramedullary nail fixation apparatus which eliminates the concentration of stress, and can effectively prohibit rotary motion of the fractured bone. Because the flexible screws are mounted inside the longitudinal center through hole of the intramedullary nail in the axial direction, equiangularly spaced from one another, and extended to different depths, no concentration of stress will occur when the flexible screws are respectively forced out of the wall of the intramedullary nail and threaded into the wall of the bone.

BRIEF DESCRIPTION OF THE DRAWINGS

The present invention will now be described by way of example with reference to the annexed drawings, in which.

DETAILED DESCRIPTION OF THE PREFERRED EMBODIMENT

Figure 6:
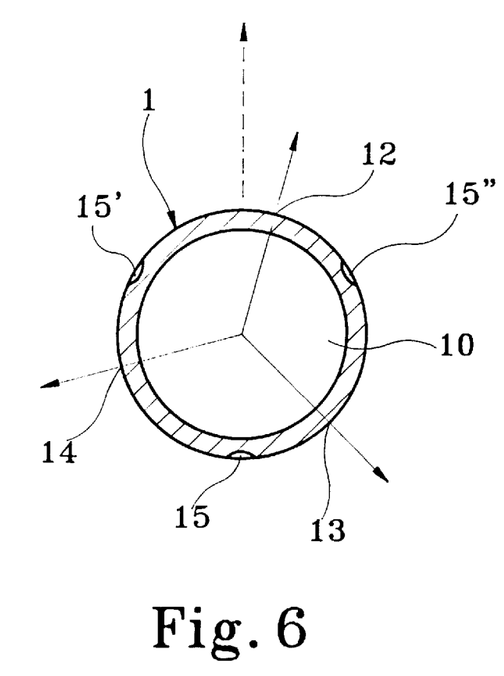
FIG. 6 is a cross sectional view of the intramedullary nail according to the present invention, showing the positions of the piercing points relative to the positions of the longitudinal grooves.
Figure 12:
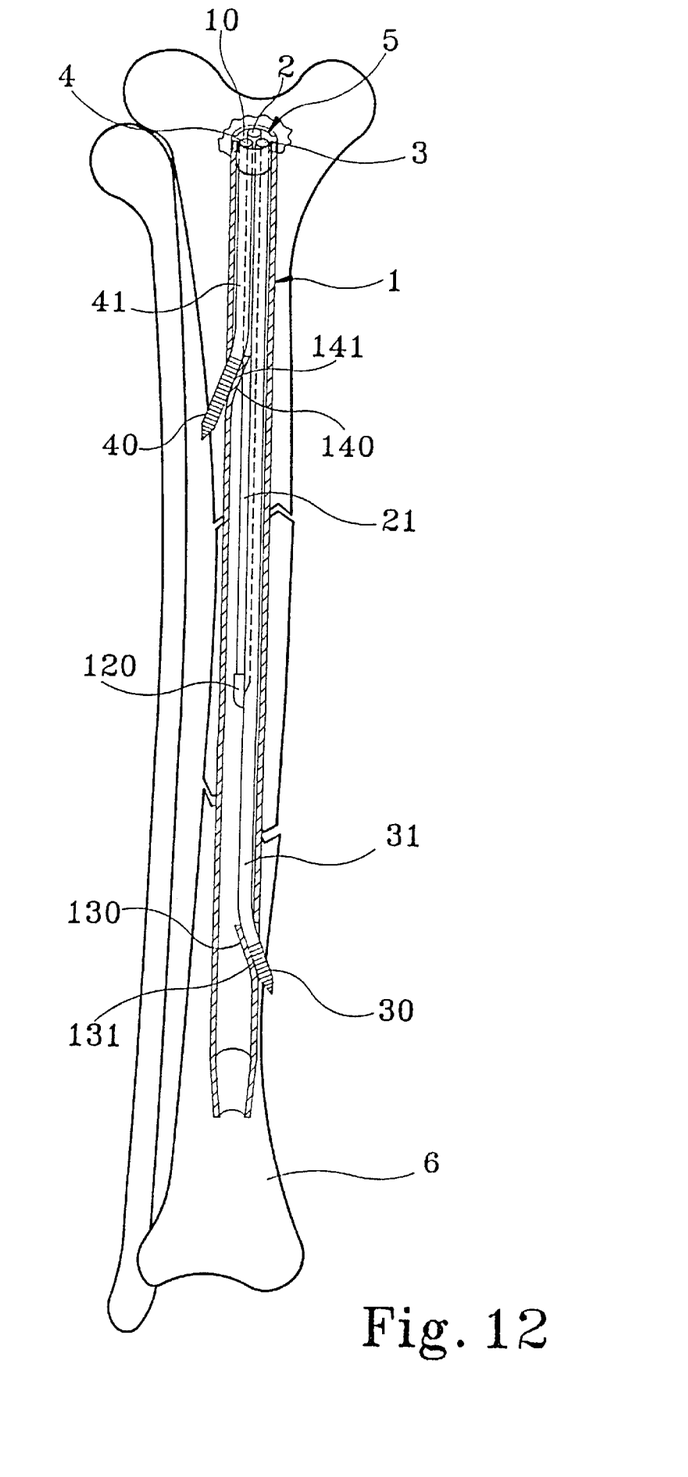
FIG. 12 is a schematic drawing showing the intramedullary nail installed in the marrow cavity of the tibia according to the present invention.

Referring to FIGS. 6 and 12, a plurality of flexible screws 2, 3, 4 are used to fix an intramedullary nail 1 in the medullary cavity of a bone. The flexible screws 2, 3, 4 are inserted into the longitudinal center through hole 10 of the intramedullary nail 1, and then radially extended out of the intramedullary nail 1 through different piercing points 12, 13, 14 at different elevations of the intramedullary nail 1, and then respectively threaded into the wall of the tibia 6 to fix the intramedullary nail 1 in place. The number of flexible the screws 2, 3, 4 depends on the type of the fracture of the piercing points and these flexible screws 2, 3, 4 must be equiangularly spaced around the cross section of the intramedullary nail 1, so that the binding points between the intramedullary nail 1 and the wall of the tibia 6 can be maintained evenly distributed in the axial direction over the periphery, to prevent the concentration of stress. If there are three flexible screws used, the intramedullary nail 1 is fixedly secured in the marrow cavity as a tripod to keep the fractured bone in the accurate length, and to prevent it from axial rotation. The shape, length, and size of the intramedullary nail are determined subject to the type of fracture of the bone. 316L stainless steel is nowadays commonly used for making intramedullary nails. The present invention will now be described by way of example in which the intramedullary nail is used to fix a fractured tibia.

Figure 1:
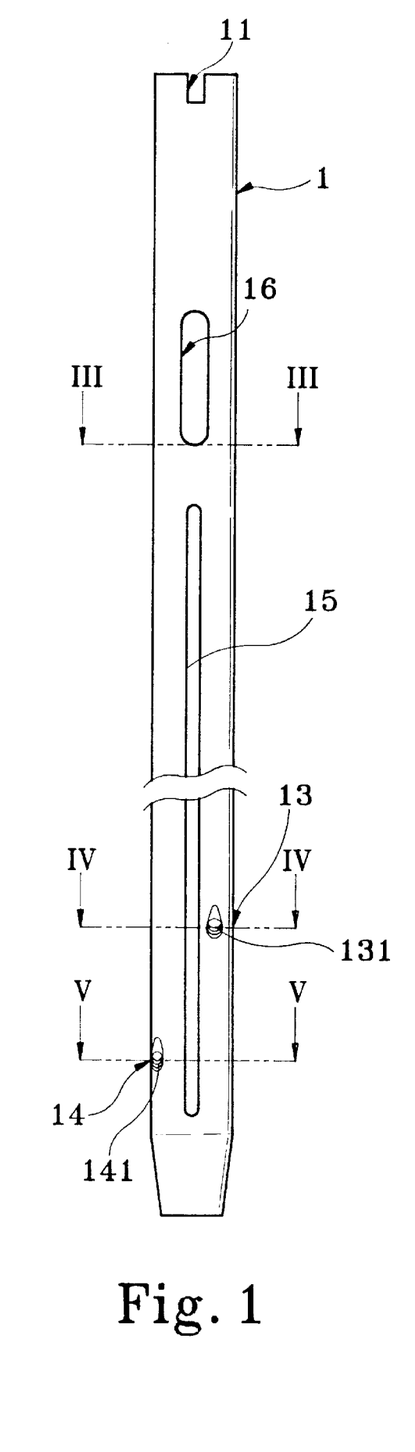
FIG. 1 shows the structure of an intramedullary nail for use in a tibia according to the present invention.
Figure 2:
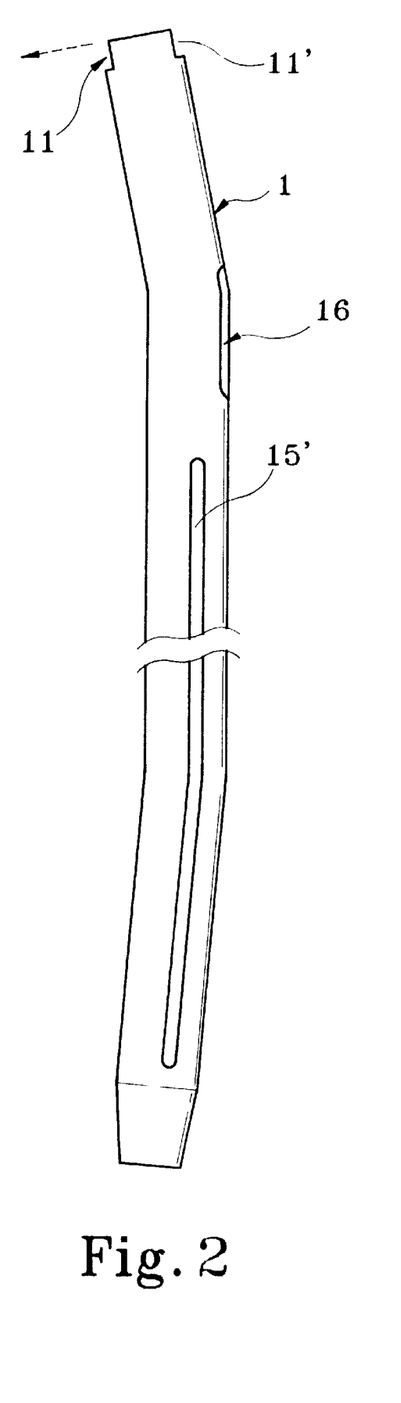
FIG. 2 is a left side view of the intramedullary nail shown in FIG. 1.
Figure 3:
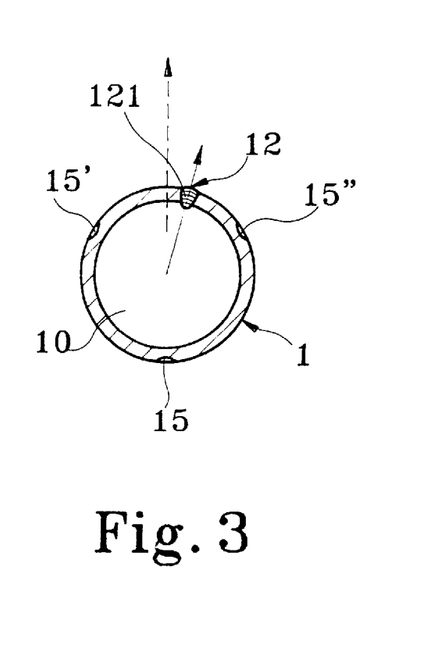
FIG. 3 is a cross sectional view taken along line III—III of FIG. 1, showing the location of the first piercing point.
Figure 4:
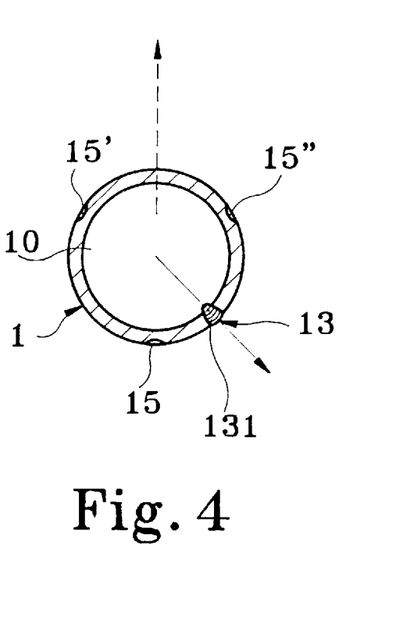
FIG. 4 is a cross sectional view taken along line IV—IV of FIG. 1, showing the location of the second piercing point.
Figure 5:
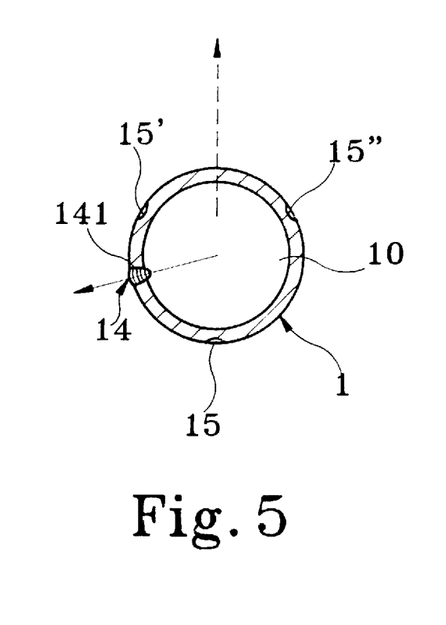
FIG. 5 is a cross sectional view taken along line V—V of FIG. 1, showing the location of the third piercing point.
Figure 10:
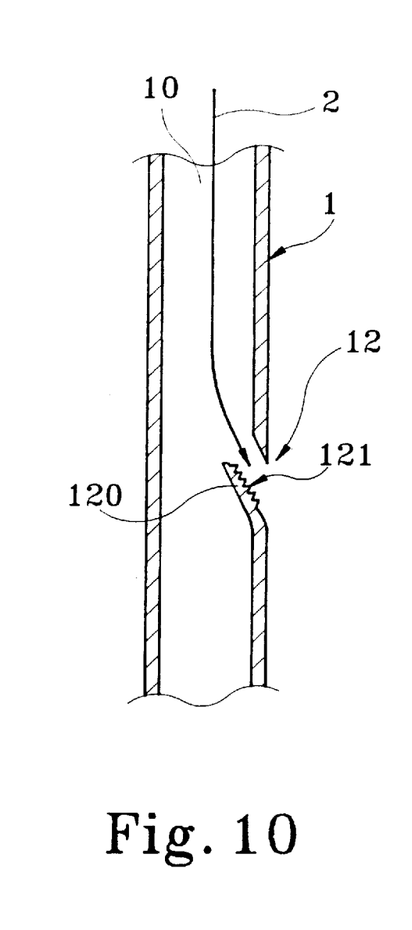
FIG. 10 is side view in section of FIG. 9.

Referring to FIGS. 1, 2, and 12, the intramedullary nail 1 is made of tubular shape defining a longitudinal center through hollow portion 10. A plurality of flexible screws, for example three flexible screws 2, 3, 4 are used to fix the intramedullary nail 1 in position after it is implanted in the marrow cavity of the tibia 6. A fixing cap 5 is fixed to the top end of the intramedullary nail 1 to protect the flexible screws 2, 3, 4. The intramedullary nail 1 has a plurality of piercing points 12, 13, 14 at the wall thereof for permitting the flexible screws 2, 3, 4 to pierce through respectively (see FIGS. 1, 3, 4, 5). The piercing points 12, 13, 14 are disposed axially at different locations, and equiangularly spaced around the cross section of the intramedullary nail 1. The wall of the intramedullary nail 1 forms a plurality of inwardly projecting tongues 120, 130, 140 at the piercing points 12. 13, 14 ( see FIGS. 10 and 12), and female threads 121, 131, 141 are respectively made on the tongues 120, 130, 140 for engagement with the self-tapping screw tips 20, 30, 40 of the flexible screws 2, 3, 4 (see also FIGS. 1, 3, 4, 5, 9, 10, 11 and 12). Therefore, the flexible screws 2, 3, 4 can be guided out of the wall of the intramedullary nail 1 by the female threads 121, 131, 141 and then fastened to the tibia 6. When installed, the flexible screws 2, 3, 4 are engaged with the female threads 121, 131, 141 to fixedly secure the intramedullary nail 1 to the tibia 6.

Figure 7:
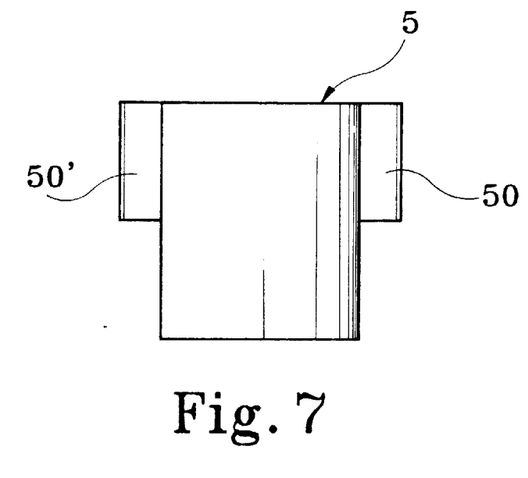
FIG. 7 is a front view of a fixing cap according to the present invention.
Figure 8:
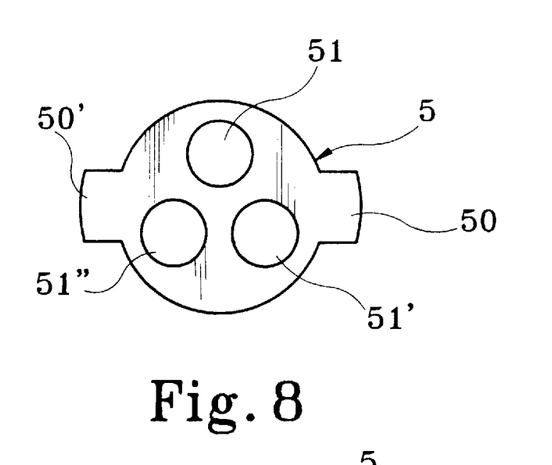
FIG. 8 is a top view of the fixing cap shown in FIG. 7.
Figure 9:
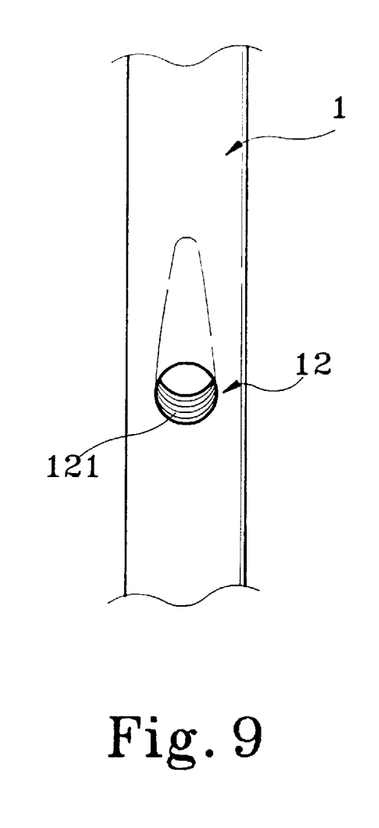
FIG. 9 is a partial view of the intramedullary nail shown in FIG. 1, showing the structure of the tongue at one piercing point.

The fixing cap 5 which is made from UHMWPE is fastened to the top end of the intramedullary nail 1 and partially engaged into the inside of thereof, comprising a plurality of key portions 50, 50' radially raised from the periphery respectively forced into engagement with respective notches 11, 11' (see FIGS. 1 and 2) at the top end of the intramedullary nail 1 to prohibit the intramedullary nail 1 from rotary motion, and a plurality of through holes 51, 51', 51" which hold the heads of the flexible screws 2, 3, 4 respectively, and prevent ingrowth of human tissues (see FIGS. 7 and 8). The intramedullary nail 1 further comprises a plurality of longitudinal grooves 15, 15', 15" (FIG. 6) equiangularly spaced around the periphery at locations away from the piercing points 12, 13, 14 to reinforce the positioning of the intramedullary nail 1 in the marrow cavity.

Figure 11:
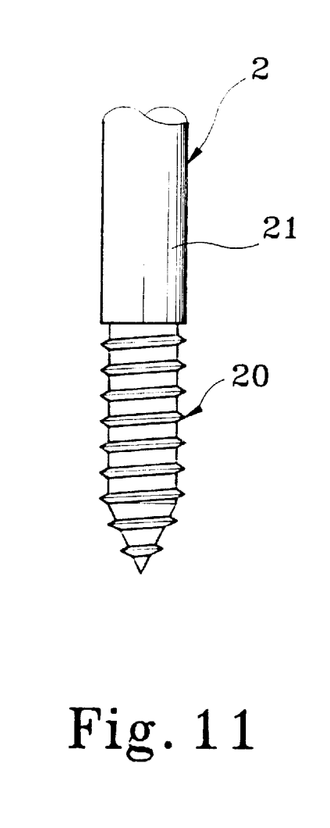
FIG. 11 shows the self-tapping screw tip of one flexible screw according to the present invention.

As shown in FIGS. 11 and 12, the flexible screws 2, 3, 4 have a respective stem 21, 31, 41 received inside the longitudinal center through hole 10 of the intramedullary nail 1, and a respective self-tapping screw tip 20, 30, 40 at the end of the respective stem 21, 31, 41. The flexible screws 2, 3, 4 are installed in the longitudinal center through hole 10 of the intramedullary nail 1 when the intramedullary nail 1 is made. The stems 21, 31, 41 of the flexible screws 2, 3, 4 are made of rounded shape, and therefore they can be rotated within the longitudinal center through hole 10 of the intramedullary nail 1 to force the self-tapping screw tips 20, 30, 40 into engagement with the female threads 121, 131, 141 of the tongues 120, 130, 140.

Figure 13:
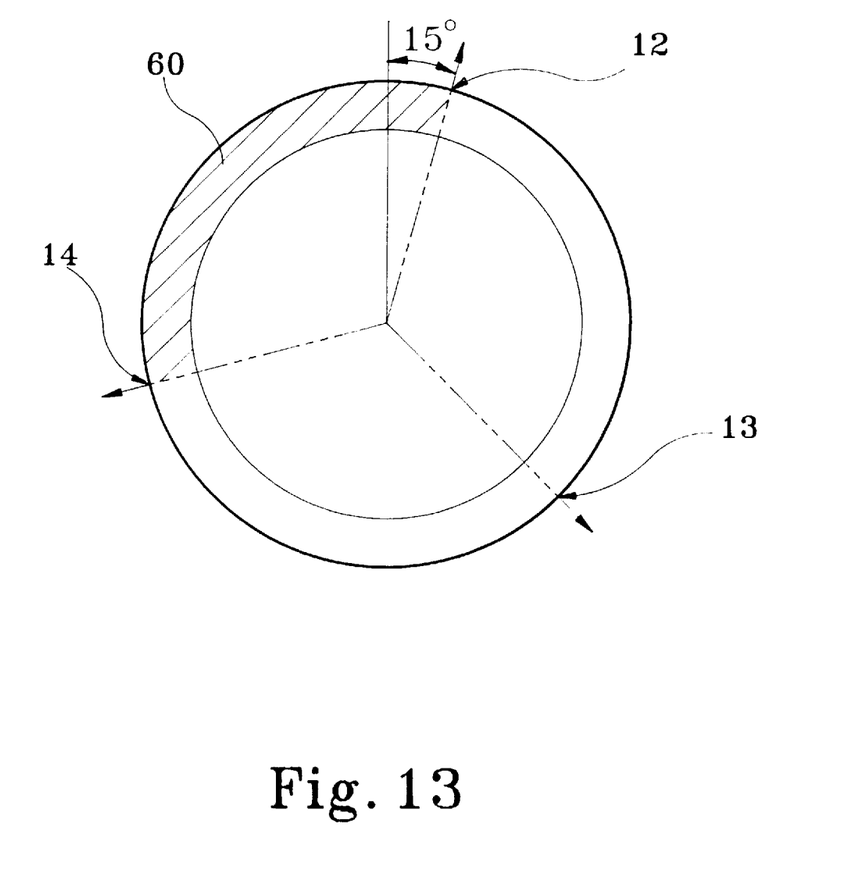
FIG. 13 is a schematic drawing showing the piercing directions of the flexible screws through the cross section of the tibia according to the present invention.

Referring to FIGS. 12 and 13, it is not advisable to thread the self-tapping screw tips 20, 30, 40 of the flexible screws 2, 3, 4 through the 120° sector area 60 at the front left side of the tibia 6. This sector area 60 is not covered with any muscle. If the self-tapping screw tips 20, 30, 40 of the flexible screws 2, 3, 4 are threaded into this sector area 60 and partially project out of the wall of the tibia 6, they may hurt the skin, or cause a pain to the nearby area. The best piercing position of the first flexible screw 2 is at 15° rightward from the front side of the tibia 6.

Before the fixation of the intramedullary nail 1, an aiming rod must be used and inserted through the guide slot 16 (see FIGS. 1 and 2) near the top end of the intramedullary nail 1 into the marrow cavity, so that the intramedullary nail 1 can be accurately guided into the marrow cavity of the bone. When the intramedullary nail 1 is set into position, the aiming rod is taken away, and then the flexible screws 2, 3, 4 are removed from the intramedullary nail 1 or threaded into the wall of the bone to fix the intramedullary nail 1 in the marrow cavity. The fixation or removal of the flexible screws 2, 3, 4 is determined subject to the type of fracture of the bone.

Figure 14:
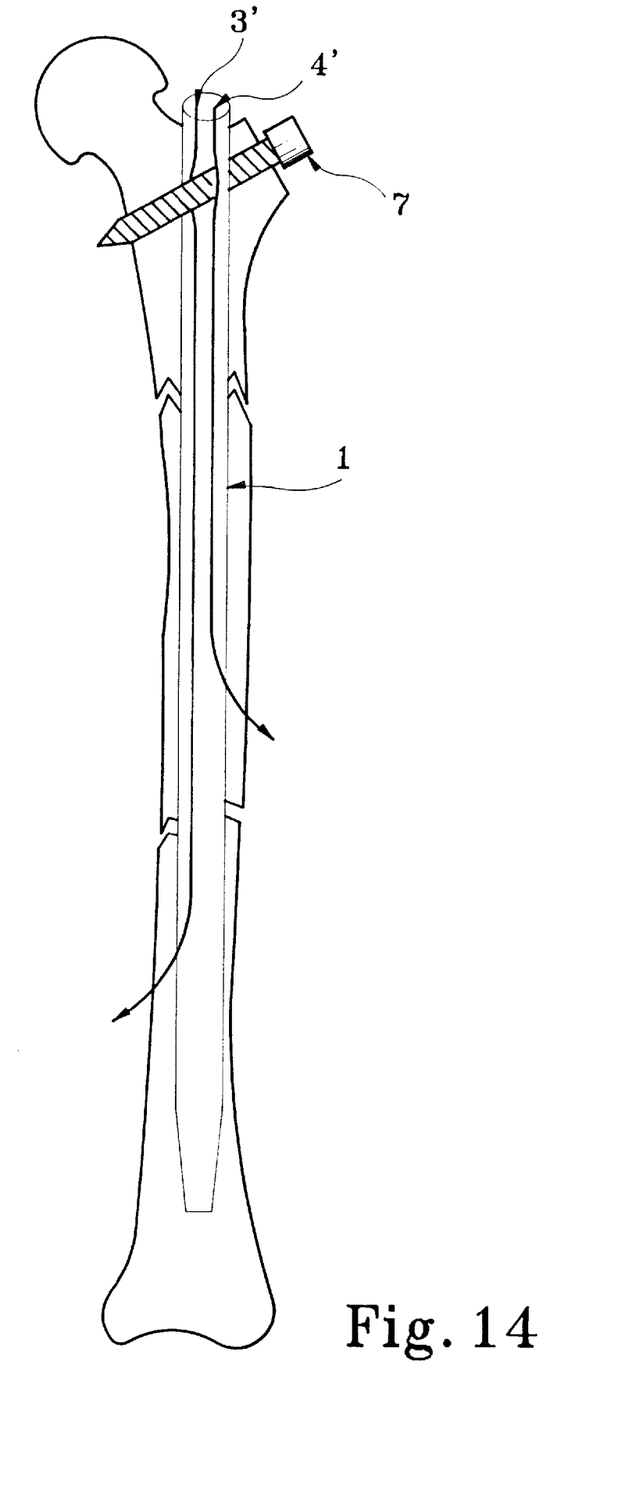
FIG. 14 is a schematic drawing of an alternative form of the present invention, showing two flexible screws and a locking screw fixed to the intramedullary nail and the bone.

FIG. 14 shows an alternative form of the present invention, in which a conventional locking screw 7 is used with two flexible screws 3', 4' to fix the intramedullary nail 1 in the marrow cavity of the bone. The conventional locking screw 7 is threaded into the proximal end of the bone (adjacent to the point through which the intramedullary nail 1 is inserted into the bone) through the intramedullary nail 1 in the radial direction to fix the intramedullary nail 1 in place, and to hold down the flexible screws 3', 4' against reverse rotation.

As indicated above, the present invention uses a tubular intramedullary nail to fix the fracture bone, and a plurality of flexible screws to fix the tubular intramedullary nail in place. The said method and technology can be applied to femur and long born of upper extremity as well.

Any modifications or variations of the present invention made by persons skilled in the art who have understood the technology and method shall be fallen into the range of claims of present invention.

I claim:

1. An intramedullary nail fixation apparatus comprising:
   an intramedullary nail for insertion into a marrow cavity of a bone, said intramedullary nail comprising a center through hole extending longitudinally along the intramedullary nail, and at least one piercing point opening communicating with the center through hole; and
   at least one flexible screw mounted in and extending along at least a portion of the center through hole of said intramedullary nail, each flexible screw comprising a rounded stem and a self-tapping screw tip at one end of said rounded stem, said self-tapping screw tip extending out of said intramedullary nail through the at least one piercing point opening and enabling the self-tapping screw tip to be threaded into a wall of a bone in which the intramedullary nail is located upon rotation of the respective flexible screw.

2. The intramedullary nail fixation apparatus of claim 1 comprising a plurality of piercing point openings wherein said piercing point openings are equiangularly spaced around a periphery of the intramedullary nail at different elevations.

3. The intramedullary nail fixation apparatus of claim 1 wherein each piercing point opening comprises a tongue formed on a wall of said intramedullary nail and projecting inwardly toward a central axis of said intramedullary nail, and a female thread formed on said tongue in engagement with the self-tapping screw tip of the at least one flexible screw for guiding said flexible screw tip out of said intramedullary nail.

4. The intramedullary nail fixation apparatus of claim 1 wherein said intramedullary nail further comprises a plurality of longitudinal grooves equiangularly spaced around the periphery.

5. The intramedullary nail fixation apparatus of claim 1 further comprising a fixing cap fixed to said intramedullary nail at one end to protect said flexible screws, said fixing cap having a plurality of through holes for holding and spacing said flexible screws in said intramedullary nail respectively.

6. The intramedullary nail fixation apparatus of claim 5 wherein said intramedullary nail further comprises a plurality of notches equiangularly spaced around a top end thereof, and wherein said fixing cap comprises a plurality of key portions equiangularly extending therefrom and engaging the notches in the top of said intramedullary nail.

7. An intramedullary nail fixation method including the steps of:
  (a) preparing a tubular intramedullary nail and mounting a plurality of flexible screws in said tubular intramedullary nail such that the plurality of flexible screws extending along a central opening extending longitudinally along the intramedullary nail;
  (b) inserting said tubular intramedullary nail into a marrow cavity of a bone; and
  (c) guiding said flexible screws radially outwards, causing said flexible screws to pass radially out of said intramedullary nail and to thread into a wall of the bone, so as to fixedly secure said intramedullary nail in the marrow cavity of the bone.

8. The intramedullary nail fixation method of claim 7 comprising the further step of guiding said flexible screws radially out of said intramedullary nail at different locations which are equiangularly spaced around a periphery of said intramedullary nail at different elevations.

9. The intramedullary nail fixation method of claim 7 further comprising the step of placing a locking screw threaded into a proximal end of the bone through said intramedullary nail to fix said intramedullary nail in place, and to hold down said flexible screws against reverse rotation.

* * * * *